(12) United States Patent
Shiku et al.

(10) Patent No.: US 8,586,023 B2
(45) Date of Patent: Nov. 19, 2013

(54) CELL CAPABLE OF EXPRESSING EXOGENOUS GITR LIGAND

(75) Inventors: Hiroshi Shiku, Tsu (JP); Hiroaki Ikeda, Tsu (JP); Jun Mitsui, Tsu (JP); Yuki Takenaka, Tsu (JP); Junichi Mineno, Otsu (JP); Ikunoshin Kato, Otsu (JP)

(73) Assignees: Mie University, Mie (JP); Takara Bio Inc., Shiga (JP)

( * ) Notice: Subject to any disclaimer, the term of this patent is extended or adjusted under 35 U.S.C. 154(b) by 0 days.

(21) Appl. No.: 13/062,999

(22) PCT Filed: Sep. 11, 2009

(86) PCT No.: PCT/JP2009/065938
§ 371 (c)(1),
(2), (4) Date: Mar. 9, 2011

(87) PCT Pub. No.: WO2010/030002
PCT Pub. Date: Mar. 18, 2010

(65) Prior Publication Data
US 2011/0250230 A1 Oct. 13, 2011

(30) Foreign Application Priority Data

Sep. 12, 2008 (JP) .................. 2008-234812
May 12, 2009 (JP) .................. 2009-115589

(51) Int. Cl.
*A61K 48/00* (2006.01)
(52) U.S. Cl.
USPC ....................... 424/93.2; 424/93.1
(58) Field of Classification Search
None
See application file for complete search history.

(56) References Cited

U.S. PATENT DOCUMENTS

| 5,750,102 A * | 5/1998 | Eisenbach et al. ......... 424/93.21 |
| 8,388,955 B2 * | 3/2013 | Lazar et al. ................ 424/130.1 |
| 2003/0049696 A1 | 3/2003 | Norment et al. |
| 2005/0014224 A1 | 1/2005 | Collins et al. |
| 2006/0099171 A1 * | 5/2006 | Tone et al. ................... 424/85.1 |

OTHER PUBLICATIONS

Gurney et al., Current Biology, 9(4):215-218, 1999.*
Zhou et al., Proceedings of the National Academy of Sciences, 105(14):5465-5470, Apr. 2008.*
Bossen et al., The Journal of Biological Chemistry, 281(20): 13964-13971, 2006.*
H. Igarashi et al., "GITR ligand-costimulation activates effector and regulatory functions of CD4+ T cells," Biochemical and Biophysical Research Communications, vol. 369, No. 4, pp. 1134-1138, 2008.
B. Calmels et al., "Bypassing tumor-associated immune suppression with recombinant adenovirus constructs expressing membrane bound or secreted GITR-L," Cancer Gene Therapy, vol. 12, pp. 198-205, 2005.
K. Baltz et al., "Cancer immunoediting by GITR (glucocorticoid-induced TNF-related protein) ligand in humans: NK cell/tumor cell interactions," The FASEB Journal: Research Communications, vol. 21, pp. 2442-2454, 2007.
P. Hu et al., "Construction and Preclinical Characterization of Fc-mGITRL for the Immunotherapy of Cancer," Cancer Therapy: Preclinical, vol. 14, No. 2, pp. 579-588, 2008.
J. Simons et al., "Induction of Immunity to Prostrate Cancer Antigens: Results of a Clinical Trial of Vaccination with Irradiated Autologuos Prostrate Tumor Cell Engineered to Secrete Granulocyte-Macrophage Colony-stimulating Factor Using ex Vivo Gene Transfer," Cancer Research, vol. 59, pp. 5160-5168, 1999.
W. Nelson et al., "Cancer cells engineered to secrete granulocyte-macrophage colony-stimulating factor using ex vivo gene transfer as vaccines for the treatment of genitourinary maliganicies," Cancer Chemotherapy Pharmacology, vol. 46, pp. S67-S72, 2000.
S. Sakaguchi et al., "Immunologic tolerance maintained by CD25+CD4+ regulatory T cells: their common role in controlling autoimmunity, tumor immunity, and transplantation tolerance," Immunological Reviews, vol. 182, pp. 18-32, 2001.
R. McHugh et al., "CD4+ CD25+ Immunoregulatory T Cells: Gene Expression Analysis Reveals a Functional Role for the Glucocorticoid-Induced TNF Receptor," Immunity, vol. 16, No. 2, pp. 311-323, 2002.
Nocentini, Giuseppe, et al., "Glucocorticoid-Induced Tumor Necrosis Factor Receptor-Related (GITR)-Fc Fusion Protein Inhibits GITR Triggering and Protects from the Inflammatory Response after Spinal Cord Injury", Molecular Pharmacology, vol. 73, No. 6, 2008, pp. 1610-1621.

* cited by examiner

*Primary Examiner* — Marianne P Allen
(74) *Attorney, Agent, or Firm* — Wenderoth, Lind & Ponack, L.L.P.

(57) ABSTRACT

Disclosed are: a cell capable of expressing an exogenous GITRL or an exogenous GITRL derivative; a method for producing the cell; a therapeutic or prophylactic agent comprising the cell as an active ingredient; use of the cell in the manufacture of a therapeutic or prophylactic agent; a method comprising a step of administering the cell to a subject; a viral vector carrying a gene encoding a GITRL or a GITRL derivative; a therapeutic or prophylactic agent comprising the viral vector as an active ingredient; use of the viral vector in the manufacture of a therapeutic or prophylactic agent; and a method comprising a step of administering the viral vector to a subject.

8 Claims, 11 Drawing Sheets

Fig.1
Fig.2
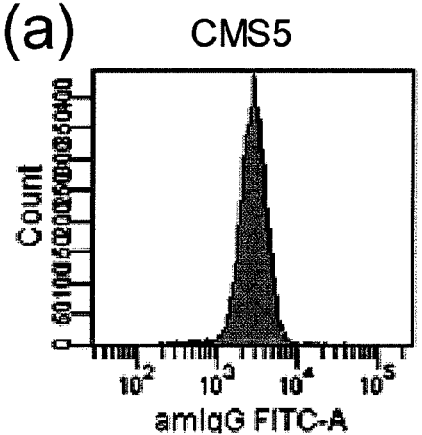
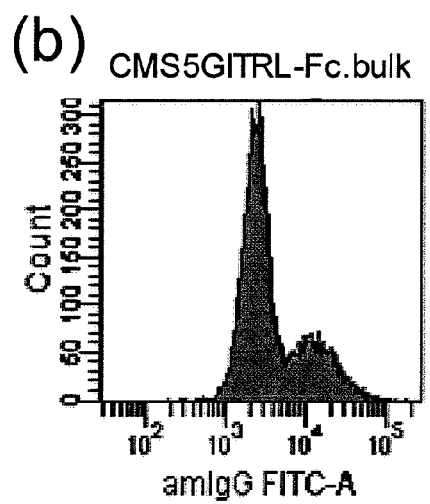 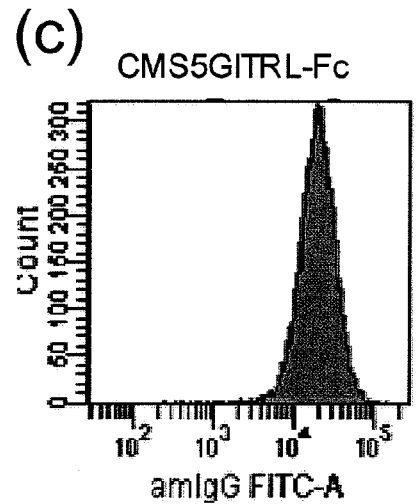

Fig.6
X ray irradiation-inactivated CMS5
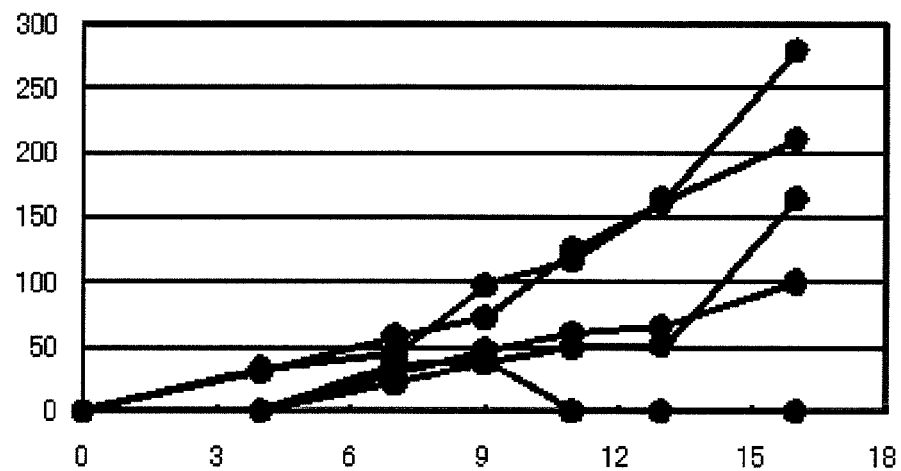
X ray irradiation-inactivated clone 1
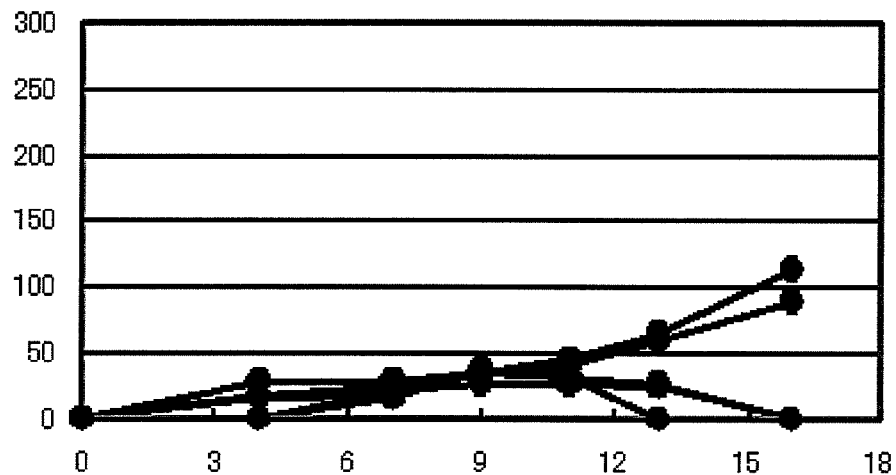

Fig.7
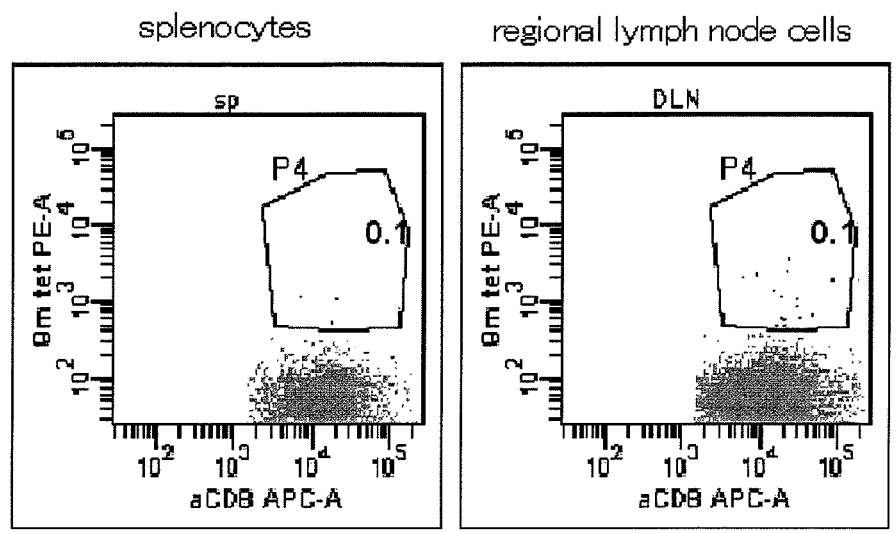
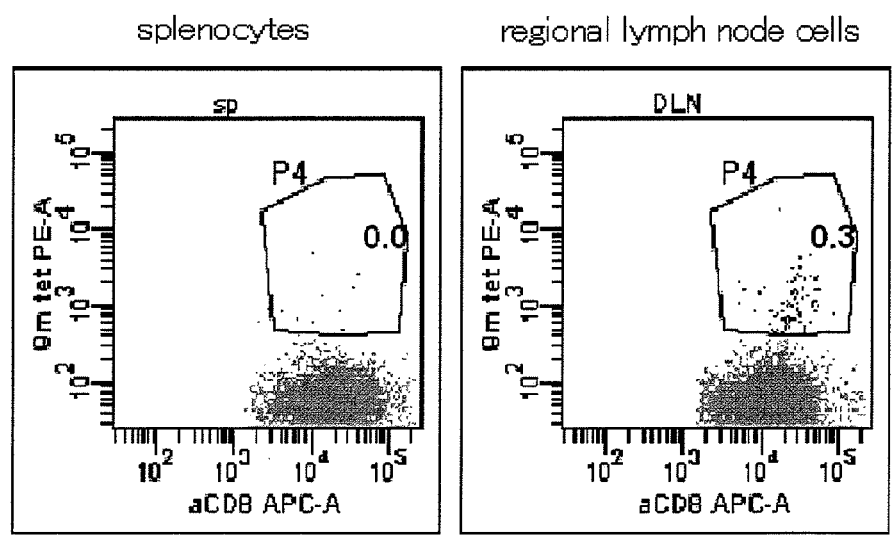

```
SEQUENCE LISTING

<160> NUMBER OF SEQ ID NOS: 7

<210> SEQ ID NO 1
<211> LENGTH: 29
<212> TYPE: DNA
<213> ORGANISM: Artificial Sequence
<220> FEATURE:
<223> OTHER INFORMATION: Synthetic construct; mGITRL-FLF primer

<400> SEQUENCE: 1
aaagatatca ctcaagccaa ctgccatcg                              29

<210> SEQ ID NO 2
<211> LENGTH: 28
<212> TYPE: DNA
<213> ORGANISM: Artificial Sequence
<220> FEATURE:
<223> OTHER INFORMATION: Synthetic construct; mGITRL-FLR primer
```

-continued

<400> SEQUENCE: 2
aaaagatcta gagatgaatg gtagatca                                              28

<210> SEQ ID NO 3
<211> LENGTH: 31
<212> TYPE: DNA
<213> ORGANISM: Artificial Sequence
<220> FEATURE:
<223> OTHER INFORMATION: Synthetic construct; mGF5 primer

<400> SEQUENCE: 3
ccgcggccgc agatctccat gtacaggatg c                                          31

<210> SEQ ID NO 4
<211> LENGTH: 31
<212> TYPE: DNA
<213> ORGANISM: Artificial Sequence
<220> FEATURE:
<223> OTHER INFORMATION: Synthetic construct; mFc3 primer

<400> SEQUENCE: 4
atgcgttaac gtcgactcat ttacccagag a                                          31

<210> SEQ ID NO 5
<211> LENGTH: 9
<212> TYPE: PRT
<213> ORGANISM: Artificial Sequence
<220> FEATURE:
<223> OTHER INFORMATION: Synthetic construct; Epitope peptide 9m

<400> SEQUENCE: 5

Gln Tyr Ile His Ser Ala Asn Val Leu
1               5

<210> SEQ ID NO 6
<211> LENGTH: 177
<212> TYPE: PRT
<213> ORGANISM: Homo sapiens

<400> SEQUENCE: 6

Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
                20                  25                  30

Val Met Leu Leu Phe Leu Cys Ser Phe Ser Trp Leu Ile Phe Ile Phe
            35                  40                  45

Leu Gln Leu Glu Thr Ala Lys Glu Pro Cys Met Ala Lys Phe Gly Pro
        50                  55                  60

Leu Pro Ser Lys Trp Gln Met Ala Ser Ser Glu Pro Pro Cys Val Asn
65                  70                  75                  80

Lys Val Ser Asp Trp Lys Leu Glu Ile Leu Gln Asn Gly Leu Tyr Leu
                85                  90                  95

Ile Tyr Gly Gln Val Ala Pro Asn Ala Asn Tyr Asn Asp Val Ala Pro
                100                 105                 110

Phe Glu Val Arg Leu Tyr Lys Asn Lys Asp Met Ile Gln Thr Leu Thr
            115                 120                 125

Asn Lys Ser Lys Ile Gln Asn Val Gly Gly Thr Tyr Glu Leu His Val
        130                 135                 140

Gly Asp Thr Ile Asp Leu Ile Phe Asn Ser Glu His Gln Val Leu Lys
145                 150                 155                 160

```
Asn Asn Thr Tyr Trp Gly Ile Ile Leu Leu Ala Asn Pro Gln Phe Ile
            165                 170                 175
Ser

<210> SEQ ID NO 7
<211> LENGTH: 748
<212> TYPE: DNA
<213> ORGANISM: Homo sapiens

<400> SEQUENCE: 7
catgacattg catccttcac ccatcacttg tgaattttttg ttttccacag ctctcatttc      60
tccaaaaatg tgtttgagcc acttggaaaa tatgccttta agccattcaa gaactcaagg     120
agctcagaga tcatcctgga agctgtggct cttttgctca atagttatgt tgctatttct     180
ttgctccttc agttggctaa tctttatttt tctccaatta gagactgcta aggagccctg     240
tatggctaag tttggaccat taccctcaaa atggcaaatg gcatcttctg aacctccttg     300
cgtgaataag gtgtctgact ggaagctgga gatacttcag aatggcttat atttaattta     360
tggccaagtg gctcccaatg caaactacaa tgatgtagct ccttttgagg tgcggctgta     420 taaaacaaa gacatgatac aaactctaac aaacaaatct aaaatccaaa atgtaggagg     480
gacttatgaa ttgcatgttg gggacaccat agacttgata ttcaactctg agcatcaggt     540
tctaaaaaat aatacatact ggggtatcat tttactagca aatccccaat tcatctccta     600
gagacttgat ttgatctcct cattcccttc agcacatgta gaggtgccag tgggtggatt     660
ggagggagaa gatattcaat ttctagagtt tgtctgtcta caaaaatcaa cacaaacaga     720
actcctctgc acgtgaattt tcatctat                                        748
```

CELL CAPABLE OF EXPRESSING EXOGENOUS GITR LIGAND

This application is a U.S. national stage of International Application No. PCT/JP2009/065938 filed Sep. 11, 2009.

TECHNICAL FIELD

The present invention relates to genetically modified cells capable of expressing a ligand for glucocorticoid-induced tumor necrosis factor receptor (hereinafter referred to as "GITR") and to such cells capable of expressing a derivative of the ligand, for use as a therapeutic or prophylactic agent, such as vaccine, for treating tumors. The present invention further relates to control of enhanced cell-mediated immune response induced by GITR-ligand-expressing cells or cells expressing a derivative of the ligand, and of immunosuppression mediated by regulatory T cells.

BACKGROUND ART

Living organisms are mainly protected from foreign material by immune response. The immune system is comprised of a variety of cells and soluble factors produced therefrom. Among those cells, leukocytes, particularly lymphocytes, play a central role in the system. Lymphocytes are grouped into two major classes, B lymphocytes (hereinafter may be referred to as "B cells") and T lymphocytes (hereinafter may be referred to as "T cells"). Cells of both classes can recognize antigens in a specific manner and interact with them to protect a living organism.

Immunotherapy has recently drawn attention as a forth method following surgery, chemotherapy and radiation therapy for treating tumors. Since immunotherapy utilizes the immunity inherent to humans, it is said that the physical burden on patients are less in immunotherapy than those in other therapies. The therapeutic approaches known as immunotherapies include: cell transfer therapy in which cells such as lymphokine-activated cells, natural killer T-cells or γδT cells obtained, for example, from exogenously-induced cytotoxic T-lymphocytes (CTLs) or peripheral blood lymphocytes by expansion culture using various method are transferred; dendritic cell-transfer therapy or peptide vaccine therapy by which in vivo induction of antigen-specific CTLs is expected; Th1 cell therapy; and immune gene therapy in which genes expected to have various effects are introduced ex vivo into the above-mentioned cells to transfer them in vivo. In these immunotherapies, CD4-positive T cells and CD8-positive T cells have traditionally known to play a critical role.

CD8-positive T cells are major effector cells that are capable of directly destroying tumor cells in vivo and in vitro. These cells are strictly specific to antigen peptides presented by MHC Class I molecules. In contrast, antigen specificities of NKT cells are not so strict, and they are considered to be effector cells that show intrinsic immune responses.

CD4-positive T cells are considered to have a fundamental role to regulate anti-tumor immune responses through a plurality of mechanisms although they do not destroy tumors directly. CD4-positive T cells that have recognized a tumor-antigen peptide represented by MHC Class II molecules promote the activation and proliferation of CTL through the interaction with antigen-presenting cells (APCs).

In contrast, CD25-positive/CD4-positive cells (regulatory T cells: Treg) have been shown to inhibit the anti-tumor immune responses and progression of various autoimmune diseases (see Patent Document 1 and Non-Patent Document 1). Specifically, since regulatory T cells suppress the activity of cytotoxic CD8-positive T cells through the control of the helper function by targeting CD4-positive T cells, some tumors are considered to utilize this system for their proliferation, thereby avoiding attack of the immune system.

GITR, which has been found as a gene expressed in regulatory T cells (see Non-Patent Document 1), is a cell surface transmembrane protein receptor and a member of the tumor necrosis factor receptor (TNFR) superfamily. GITR has been shown to be constitutively present on non-activated T cells. GITR binds to another transmembrane protein referred to as GITR ligand (hereinafter referred to as "GITRL"). Agonistic antibodies against GITR have been shown to abrogate the immunosuppressant activity of regulatory T cells, suggesting that GITRL plays a functional role in regulating the activity of regulatory T cells via GITR (see Non-Patent Document 2).

PRIOR ART DOCUMENTS

Patent Document

Patent Document 1: US 2003049696

Non Patent Documents

Non Patent Document 1: S. Sakaguchi et al., Immunol. Rev. 182 (2001), pp 18-32
Non Patent Document 2: McHugh et al., Immunity 16 (2002), PP 311-23

SUMMARY OF THE INVENTION

Problems to be Solved by the Invention

In view of the present situation described, the present invention aims to provide a material that has an immune system enhancing effect with wide utility and is useful as a therapeutic agent or prophylactic agent (vaccine), and a method for treating subjects to whom the material is applied.

Means for Solving the Problems

The present inventors have found that a potent anti-tumor vaccine effect and a local anti-tumor cell-mediated immune response are induced by administration of cells modified to express GITRL or a GITRL derivative to living organisms. Based on this finding, the present invention has been completed.

That is, the present invention relates to:

[1] a cell capable of expressing exogenous GITRL (Glucocorticoid-Induced Tumor necrosis factor Receptor Ligand) or an exogenous GITRL derivative;

[2] the cell of [1], wherein the derivative is a fusion protein of GITRL or a GITRL fragment and an Fc fragment of an immunoglobulin (GITRL-Fc);

[3] the cell of [1] or [2], wherein the cell is a tumor cell or an immune cell;

[4] the cell of [3], wherein the cell is an inactivated tumor cell;

[5] a method for producing the cell of [1], comprising transforming the cell with a vector comprising a gene encoding GITRL or a GITRL derivative;

[6] the method of [5], wherein the derivative is GITRL-Fc;

[7] the method of [5] or [6], wherein the cell is a tumor cell or an immune cell;

[8] the method of [7], wherein the cell is an inactivated tumor cell;

[9] a virus vector comprising gene encoding GITRL or a GITRL derivative;

[10] the virus vector of [9], wherein the vector is selected from the group consisting of retrovirus vectors, adenovirus vectors, adeno-associated virus vectors and Sendai virus vectors, and comprises a gene encoding GITRL or a GITRL derivative;

[11] a therapeutic or prophylactic agent comprising the cell of any one of [1] to [4] as an active ingredient;

[12] use of the cell of any one of [1] to [4] in the manufacture of the therapeutic or prophylactic agent of [11];

[13] a method for treating a subject, comprising administering the cell of any one of [1] to [4] to the subject;

[14] a therapeutic or prophylactic agent comprising the virus vector of [9] or [10] as an active ingredient;

[15] use of the virus vector of [9] or [10] in the manufacture of the therapeutic or prophylactic agent of [14]; and

[16] a method for treating a subject, comprising administering the virus vector of [9] or [10] to the subject.

Effect of the Invention

Provided by the present invention are: a cell capable of exhibiting a potent anti-tumor vaccine effect and an effect of inducing an immune response to a particular antigen; a therapeutic or prophylactic agent comprising the cell as an active ingredient; and a method for treating a subject to whom the cell is applied.

BRIEF DESCRIPTION OF THE DRAWINGS

FIG. 1 shows a schematic illustration of pMT-mGFc.
FIG. 2 shows the results of measurements from mouse GITRL-Fc; (a) non-transfected cells; (b) mouse GITRL-Fc gene-transfected bulk cells; and (c) clone 1.
FIG. 6 shows chronological changes in mouse tumor size.
FIG. 7 shows the results of a tetramer assay.

MODE FOR CARRYING OUT THE INVENTION

Figure 3:
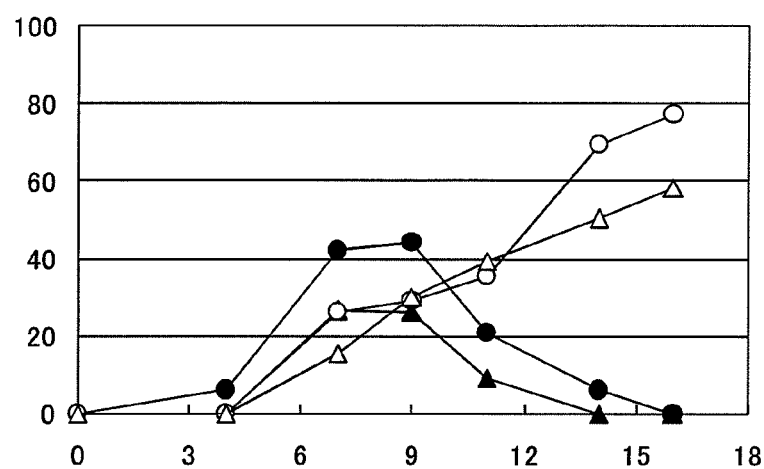
FIG. 3 shows chronological changes in mouse tumor size.

As used herein, the term "GITRL" refers to a ligand that binds to a glucocorticoid-induced tumor necrosis factor receptor (GITR). GITRL is also referred to as TNFSF18 (tumor necrosis factor (ligand) superfamily, member 18). The amino acid sequence of human GITRL is shown in SEQ ID NO: 6 in the Sequence Listing or in Swiss Prot ID NO: Q9UNG2. The nucleotide sequence of human GITRL is shown in SEQ ID NO: 7 in the Sequence Listing or in GenBank Accession NO: NM_005092. GITRL consists of 177 amino acids and composed of the intracellular domain between positions 1-28, the transmembrane domain between positions 29-49, and the extracellular domain between positions 50-177.

As used herein, the term "a GITRL derivative" refers to (A) a fragment having a part(s) of GITRL or (B) a fusion protein comprising GITRL or a GITRL fragment, which fragment or protein is a molecule capable of interacting with GITR to transmit stimulations to GITR-expressing cells. The term "GITRL-Fc" refers to a fusion protein of GITRL or a GITRL fragment and an Fc fragment of an immunoglobulin (CH2 and CH3 regions).

As used herein, the term "exogenous GITRL" refers to a polypeptide expressed from a nucleic acid encoding GITRL which has been introduced artificially and exogenously. There may be an endogenous nucleic acid having the same sequence as that of the nucleic acid encoding exogenous GITRL in the cell into which the above-described nucleic acid is introduced. The term "an exogenous GITRL derivative" refers to a polypeptide expressed from a nucleic acid encoding a GITRL derivative which has been introduced artificially and exogenously.

As used herein, the term "inactivation treatment" refers to carrying out a treatment for making cells unable to proliferate. This treatment allows to obtain cells that are unable to undergo subsequent mitosis but still retains the capability to express the protein (e.g., GITRL or a GITRL derivative, a cytokine, or a tumor antigen) which has been expressed prior to the treatment. As described below, the inactivation treatment may be carried out by various methods known to one skilled in the art. The inactivation treatment is a treatment that inhibits the proliferation by at least about 90%, preferably about 95% or more preferably substantially 100% of cells.

The term "autologous" as used in the present invention refers to derivation from the same individual (i.e., self) or genetically identical individuals (i.e., autogenicity). The term "allogenic" refers to derivation from a different individual of the same species, i.e., allogenicity.

As used herein, the term "tumor cells" refers to cells showing an aberrant growth phenotype or aberrant cellular state, the cells being characterized by showing autonomous proliferation and, as a result, by uncontrollable cell proliferation. The "tumor cells" include "malignant tumor cells" and "benign tumor cells," and are also referred to as "neoplasm-derived cells." The term "tumor" refers to a mass of tumor cells or tumor cells as a whole.

As used herein, the term "expression" refers to transcription and/or translation of the coding region of an endogenous gene or transgene in a cell.

As used herein, the term "transformation" refers to introduction of an exogenous nucleic acid into a cell. For example, transformation includes introduction of an exogenous nucleic acid into a cell using a viral or non-viral vector. Various techniques for transforming mammalian cells are described, for example, by Keown et al. in Methods of Enzymology 185:527-537(1990).

(1) The Cells and Vectors of the Present Invention, and the Method for Producing the Cells of the Present Invention The present invention relates to cells capable of expressing an exogenous GITRL or an exogenous GITRL derivative, for use in treating or preventing tumors. There is no particular limitation on the expressed GITRL or the expressed GITRL derivative, as long as it is a molecule transmitting stimulations to GITR-expressing cells by interacting with GITR. A result of the transmission of stimulations is exemplified by a reduction of the immunosuppressive effect retained by GITR-expressing cells. For the production method of the present invention, the gene encoding naturally-occurring GITRL, which has the amino acid sequence shown, for example, in SEQ ID NO: 6, or its derivative may be used. The gene encoding GITRL or a GITRL derivative can be expressed as a cell membrane protein, including intracellular or cell surface-presented proteins, or secretory proteins being to be released from the cell. The cells of the present invention that are capable of expressing GITRL or a GITRL derivative are capable of localizing the GITRL or the GITRL derivative within the cell, on the cell membrane, or in the periphery of the cell, thereby reducing the systemic effects, compared to administration of GITRL per se into living organisms.

GITRL derivatives include GITRL variants with modified amino acid sequences and fragments having a part(s) of GITRL, particularly, GITRL fragments having the extracellular domain between the amino acid positions 50-177 or the part between the amino acid positions 47-177 of the amino acid sequence of human GITRL shown in SEQ ID NO: 6. A GITRL derivative may be a polypeptide encoded by a nucleic acid that hybridizes to the complementary strand of a nucleic acid having the nucleotide sequence of SEQ ID NO: 7 under stringent conditions. As used herein, the term "stringent conditions" refers to conditions wherein a nucleic acid is incubated with, for example, a probe in 6×SSC (1×SSC indicates 0.15 M of NaCl, 0.015 M of sodium citrate, pH 7.0) containing 0.5% SDS, 5×Denhardt's and 100 µg/ml denatured salmon-sperm DNA at 68° C. for 12-20 hours. DNA hybridized with the probe may be detected after washing, for example, with 0.1×SSC containing 0.5% SDS at 68° C.

GITRL derivatives include fusion proteins in which GITRL or a GITRL fragment is fused with another (other) protein(s). The fusion proteins may contain a secretory signal, an intracellular localization signal, or a tag sequence, and they are exemplified by fusion proteins fused with another protein such as a receptor, a ligand or an antibody, or its fragment. GITRL-Fc, a fusion protein of the GITRL or its fragment and an Fc fragment of an immunoglobulin may be preferably used as a GITRL derivative in terms of protein productivity and in vivo stability. Although any fragment derived from IgG, IgM, IgA, IgD or IgE may be used as an Fc fragment of an immunoglobulin, a fragment from an IgG isotype, IgG2, may be preferably used due to the low cytotoxicity. A fusion protein with an immunoglobulin Fc fragment may be prepared using a commercially available product (for example, pFUSE-h1gG2-Fc2, from InvivoGen). Although the Fc fragment of GITRL-Fc may be located either at the N terminus or C terminus of the fusion protein, a GITRL derivative having an Fc fragment at the C terminus may be preferably used.

Although there is no particular limitation on the cells used to express exogenous GITRL or an exogenous GITRL derivative, tumor cells or immune cells, for example, may preferably be used. Such tumor cells may be self-derived (autologous) tumor cells obtained from the same individual, may be a allogenic tumor cells obtained from an individual different from the subject, or may be established tumor cell lines. For such a tumor cell line, it is preferable to use a tumor cell line originated from the same type of source as a tumor or malignant tumor in need of treatment or prevention. The tumor cells of the present invention capable of expressing GITRL or a GITRL derivative may activate immune cells present in the vicinity of the tumor cells, with suppressing the activity of regulatory T cells, to potently induce the immune system against the tumor antigen present on the surface of the tumor cells.

In a preferred embodiment of the present invention, tumor cells in which expression of GITRL or a GITRL derivative has been induced are then inactivated. The inactivation treatments include physical treatments, such as irradiation of X-rays or γ-rays, and chemical treatments using chemical agents, such as mitomycin C and cyclohexamide. The inactivation treatment may be carried out, for example, but not limited to, by irradiation of X-rays with a dose of about 10 to about 1000 cGy, and more preferably about 50 to about 500 cGy, although there is no particular limitation on the inactivation treatment as long as it allows to maintain the expression of GITRL or a GITRL derivative and to suppress the proliferation of the expressing cells.

In another embodiment of the present invention, immune cells are used as cells to express GITRL or a GITRL derivative. Such available immune cells are exemplified by T cells, such as CD8-positive T cells or CD4-positive T cells, or antigen-presenting cells. These cells may be autologous immune cells, allogeneic immune cells, or established immune cell lines. When tumor treatment is contemplated, T cells expressing a T cell receptor (TCR) that recognizes a tumor antigen expressed in the tumor is preferred. T cells that express both a T-cell receptor that specifically recognizes a particular tumor antigen, and GITRL or a GITRL derivative have affinity for tumor cells; and are thus able to selectively transport the GITRL or the GITRL derivative to the tumor cells or to the periphery of the tumor cells. Therefore, the activity of regulatory T cells are suppressed and, as a result, immune cells are activated in the vicinity of tumors where the immune cells of the present invention capable of expressing GITRL or a GITRL derivative are specifically accumulated. Thus, the immune system against tumor cells expressing a particular tumor antigen can be strongly induced.

The cells of the present invention may be produced by ex vivo transformation of cells using a viral or non-viral vector comprising a nucleic acid construct in which a gene encoding GITRL or a GITRL derivative is operably linked to a regulatory element(s).

As used herein, the term "operably linked" refers to a linkage of a nucleic acid sequence with another (other) nucleic acid sequence(s) in a functional relationship. For example, if a DNA sequence encoding an RNA molecule or a protein is placed under the control of a promoter or regulatory element, or a promoter or regulatory element is placed so as to influence the expression level of a coding or structural DNA sequence, the promoter or regulatory element is considered to be "operably linked" to the DNA sequence encoding an RNA molecule or a protein.

The term "regulatory element" refers to a sequence involved in the control of expression of a nucleotide sequence. Regulatory elements include promoters, enhancers and termination codons. Regulatory elements typically also include a sequence needed for proper translation of a nucleotide sequence.

The term "promoter" refers to a non-translational DNA sequence usually located upstream of the coding region that contains the binding site for RNA polymerase and initiates transcription of the DNA into RNA. The promoter region may also contain other elements that act as regulators of gene expression.

Vectors that can be used to produce the cells of the present invention include, but not limited to, for example, viral vectors and non-viral vectors, such as retrovirus (including Lentivirus) vectors, adenovirus (Ad) vectors (including replicable forms and replication-deficient forms of the vectors), adeno-associated virus (AVV) vectors, Simian virus 40 (SV-40) vectors, herpes virus vectors, vaccinia virus vectors, Sendai virus vectors, and non-viral plasmid vectors. In addition, agents for improving the gene-transfer efficiency, such as RetroNectin® (from Takara Bio Inc.), may be used in the process of gene transfer.

Methods of gene transfer without using viral vectors include, for examples, without limiting the present invention, methods using a carrier such as liposome or ligand-polylysine, the calcium phosphate method, electroporation and particle bombardment. When these methods are used, an exogenous gene integrated into plasmid DNA, linear DNA or RNA is transferred.

Vectors expressing the gene for GITRL or a GITRL derivative that are used to produce the cells of the present invention may comprise heterologous regulatory sequences, such as constitutive promoters, inducible promoters, tumor-selective promoters and enhancers. Such promoters include, but not limited to, for example, E2F promoters, telomerase (hTERT) promoters, the cytomegalovirus enhancer/Chicken β-actin/rabbit β-globin promoter, elongation factor 1-α promoters (EF1-α promoters), glia-specific promoters, and neuron-specific promoters. As used herein, the term "enhancer" refers to a nucleotide sequence that, when it is operably linked to a coding sequence, increases the transcription of the coding sequence operably linked to a promoter as compared to the transcriptional activation achieved by the promoter alone (i.e., enhances the transcription from the promoter).

Further, in the present invention, constitutive promoters (e.g., cytomegalovirus (CMV) immediate-early promoters, RSV LTR, MoMLV LTR, the CAG promoter, the phosphoglycerate kinase-1 promoter (PGK), and SV-40 promoters) may be used. Vectors expressing the gene for GITRL or a GITRL derivative may also comprise a nucleic acid encoding a signal peptide or a tag peptide. Such vectors may or may not comprise introns. Thus, such vectors may comprise a number of transgenes, a combination of transgenes, or a combination of transgenes/regulatory elements.

The method for transforming the cells of the present invention that are capable of expressing exogenous GITRL or an exogenous GITRL derivative may comprise a step of culturing the cells before transforming them with a vector as described above or, if inactivation treatment is carried out, before carring out the inactivation treatment. Alternatively, the method may comprise a step of culturing the cells after transforming them with a vector as described above or, if inactivation treatment is carried out, before carrying out the inactivation treatment. The culture as described above may be carried out using known medium under culture conditions appropriately determined depending on the cells to be cultured.

Moreover, a vector containing the above-described nucleic acid construct which comprises a gene encoding GITRL or a GITRL derivative operably linked to a regulatory element(s) is also encompassed by the present invention. This vector is hereinafter referred to as "the vector of the present invention." The vector may be used to confer the capability of expressing GITRL or a GITRL derivative on the subject cells by administering the vector itself to the cells, as well as to produce the cells of the present invention as described above.

There is no particular limitation on the type of the vector of the present invention; a variety of viral or non-viral vectors as described above may be used. In preferred embodiments, viral vectors with high gene-transfer efficiency to cells are used. More preferably, viral vectors that can be administered directly to living organisms (to the subject) are used. Viral vectors that can be administered directly to living organisms include, without particularly limiting the present invention, retrovirus vectors, adenovirus vectors, adeno-associated virus vectors and Sendai virus vectors.

The cells of the present invention that are capable of expressing exogenous GITRL or an exogenous GITRL derivative induce immune responses of surrounding immune cells. Such immune responses induced may be evaluated in a subject by determining the tumor growth suppressive ability (for example, by measuring the tumor size) or using antigen-specific cytotoxicity assay, cell proliferation assay, cytolytic cell assay, and in vivo delayed-type hypersensitivity testing that uses a recombinant tumor-associated antigen or immunogenic fragment, or an antigen-derived peptide, before the initial administration of cells expressing GITRL or a GITRL derivative, or at various time points after the initiation of treatment. Such immune responses may also be evaluated based on the ratio of the immune cell components, such as CD8-positive T cells, CD4-positive T cells and regulatory T cells. Furthermore, it is also possible to evaluate immune responses based on the production of cytokines, such as interferon (IFN)-γ or tumor necrosis factor (TNF)-α, or on the presence of a cell-surface antigen, such as CD107a. Cells producing a plurality of cytokines or presenting a plurality of cell surface antigens are called multifunctional cells and useful for immunotherapies. Additional methods for measuring the increase in immune responses include assays usually used for measuring T cell responses, such as delayed-type hypersensitivity testing, flow cytometry using peptide-major histocompatibility complex tetramers, lymphocyte proliferation assays, enzyme-linked immunosorbent assays, enzyme-linked immunospot assays, cytokine flow cytometry, direct cytotoxicity assays, determination of cytokine mRNA by quantitative reverse transcriptase-polymerase chain reaction, and limiting dilution analysis.

(2) The Therapeutic or Prophylactic Agents of the Present Invention, and Use of the Cells or Vector in the Manufacture of the Therapeutic or Prophylactic Agents The cells of the present invention that express exogenous GITRL or an exogenous GITRL derivative and the vector comprising a nucleic acid construct in which a gene encoding GITRL or a GITRL derivative is operably linked to a regulatory element(s), both of which are described in (1) as above, may be used to produce the therapeutic or prophylactic agent of the present invention that comprises them as an active ingredient(s).

Tumor cells expressing GITRL or a GITRL derivative may be used as a therapeutic agent or prophylactic agent (cell vaccine). Without being bound by particular theory, the cells of the present invention may serve as a potent cell vaccine, since the activity of regulatory T cells is inhibited by GITRL expressed in the vicinity of tumor cells expressing the GITRL or a GITRL derivative, and the suppression on immune cells, including antigen-presenting cells, CD8-positive T cells and CD4-positive T cells, is abrogated, i.e., these cells are activated, resulting in enhancement of the immune system to these tumor cells.

Immune cells expressing GITRL or a GITRL derivative may be used as a therapeutic or prophylactic agent. Without being bound by particular theory, it is possible, for example, for T cells that express both a TCR that specifically recognizes a particular tumor antigen, and GITRL or a GITRL derivative are able to specifically transport the GITRL or the GITRL derivative to tumor cells or to the periphery of the tumor cells. Therefore, the activity of regulatory T cells is suppressed and, as a result, immune cells are activated in the vicinity of tumors where the immune cells of the present invention capable of expressing GITRL or a GITRL derivative are accumulated. Thus, the immune system against tumor cells expressing a particular tumor antigen can be strongly induced.

A vector comprising a nucleic acid construct in which a gene encoding GITRL or a GITRL derivative is operably linked to a regulatory element(s) is able to confer the capability of expressing the GITRL or the GITRL derivative on the subject cells in vivo. Accordingly, cells introduced with the vector exhibit the same function as the tumor or immune cells described above. For example, administration of the vector of the present invention into tumors has an equivalent effect to that of administration of tumor cells expressing GITRL or a GITRL derivative into tumors.

The therapeutic or prophylactic agent of the present invention is intended to treat or prevent diseases on which cells capable of expressing GITRL or a GITRL derivative are efficacious. By way of example, such diseases include tumor diseases (such as leukemia and solid tumors), and infectious diseases caused by viruses, bacteria and fungi (e.g., influenza, tuberculosis or deep mycosis). The therapeutic or prophylactic agent of the present invention is useful for, for example, eliminating or reducing tumor or infected cells or inhibiting the growth of such cells.

The therapeutic or prophylactic agent of the present invention may be administered intradermally, intramuscularly, subcutaneously, intraperitoneally, intranasally, intra-arterially, intravenously (including indwelling catheterization), intratumorally, or by intra-afferent lymphatic infusion. Furthermore, the therapeutic or prophylactic agent of the present invention is suitable for use in immunotherapy. In immunotherapy, T cells or inactivated tumor cells which is suitable for treating a subject are administered intravenously, intra-arterially, subcutaneously or intraperitoneally to the subject by, for example, injection or infusion. The therapeutic or prophylactic agent of the present invention is very useful for use in the subject as described above and may be prepared as an injection or infusion by mixing with, for example, an organic or inorganic carrier, excipient or stabilizer which is suitable for parenteral administration, according to a well-known method in the art.

The therapeutic or prophylactic agent of the present invention comprises an effective amount of cells capable of expressing exogenous GITRL or an exogenous GITRL derivative, or a vector comprising a nucleic acid construct in which a gene encoding GITRL or a GITRL derivative is operably linked to a regulatory element. As used herein, an effective amount refers to an amount of cells that show a therapeutic or prophylactic effect in subjects administered with the therapeutic or prophylactic agent as described above, compared with untreated subjects. The specific amount may vary and may be determined appropriately depending on the dosage form, the administration route, the intended use, and the age, body weight and conditions of the subjects. For example, the amount of the cells of the present invention that are capable of expressing GITRL or a GITRL derivative in the therapeutic or prophylactic agent of the present invention that comprises those cells as an active ingredient is not particularly limited. However, for example, it is preferably $1 \times 10^3$ to $1 \times 10^{11}$ cells/mL, more preferably $1 \times 10^4$ to $1 \times 10^{10}$ cells/mL and even more preferably $1 \times 10^5$ to $1 \times 10^9$ cells/mL. Also, the dose of the therapeutic or prophylactic agent of the present invention is not particularly limited. However, for example, it is preferably $1 \times 10^6$ to $1 \times 10^{12}$ cells/day, more preferably $1 \times 10^7$ to $5 \times 10^{11}$ cells/day and even more preferably $1 \times 10^8$ to $2 \times 10^{11}$ cells/day, for an adult human.

The therapeutic or prophylactic agent of the present invention may further comprise an excipient. Such excipients include: various cell culture media with or without physiologically compatible buffers, such as phosphate or Hepes, nutrients, such as dextrose, physiologically compatible ions, or amino acids (in particular, amino acids free of immunogenic components); or isotonic saline. Supported reagents, such as albumin or plasma fractions, or inert thickeners may be used.

(3) The Treatment Method of the Present Invention

The present invention relates to a method for treating a subject, comprising the step of inducing immune response by administering to a subject cells capable of expressing GITRL or a GITRL derivative, or a vector comprising a nucleic acid construct in which a gene encoding GITRL or a GITRL derivative is operably linked to a regulatory element(s).

Cells used in the method of the present invention for treating a subject may be obtained by the method described above in (1) for producing the cells of the present invention that are capable of expressing GITRL or a GITRL derivative. The cells may be cells produced by the method described above in (1) using the cells collected from the subject or other individuals as a material. The method further comprises, before the administration to the subject, the steps of culturing the cells produced and/or sorting the cells using appropriate markers.

In the method of the present invention for treating a subject, cells capable of expressing GITRL or a GITRL derivative, or a vector comprising a nucleic acid construct in which a gene encoding GITRL or a GITRL derivative is operably linked to a regulatory element, i.e., the therapeutic or prophylactic agent of the present invention that is described above in (2), is administered to a subject. As used herein, a subject is not particularly limited; however, preferably, it indicates a living organism (e.g., a human patient or non-human animal) suffered from a disease susceptible to the cells produced by the method of the present invention, or a living organism in need of prophylactic treatment against the disease.

The administration of the cells may be carried out by intradermal, intramuscular, subcutaneous, intraperitoneal, intranasal, intra-arterial, intravenous (including indwelling catheterization) or intratumoral administration, or by intra-afferent lymphatic infusion to a subject.

EXAMPLES

The present invention will be described in more detail below with examples, but the present invention is not limited to the scope of these examples.

Example 1

Construction of a Retrovirus Vector Expressing Mouse GITRL-Fc

EcoRV-mouse GITRL-BglII was obtained by extracting mRNA from the spleen of BALB/c mice (CLEA Japan, Inc.) and performing RT-PCR using the mGITRL-FLF primer shown in SEQ ID NO: 1 and the mGITRL-FLR primer shown in SEQ ID NO: 2. The PCR fragment thus obtained was cleaved with endonucleases EcoRV and BglII (Takara Bio Inc.) and cloned into the EcoRV-BglII site of pFUSE-mFc2 vector (InvivoGen), thereby generating pFuse-mFc/mGITRL. PCR was performed using pFuse-mFc/mGITRL as template, the mGF5 primer shown in SEQ ID NO: 3 and the mFc3 primer shown in SEQ ID NO: 4. The amplified product thus obtained was cloned into the pCR-Blunt vector (Invitrogen), thereby generating pCRblunt-mGFc. The mouse GITRL-Fc portion obtained by digesting pCRblunt-mGFc with endonucleases NotI and SalI (Takara Bio Inc.) was excised and cloned into the NotI-SalI site of the pMIN vector [Gene Therapy, Vol. 7, pp. 797-804 (2000)], thereby generating pMT-mGFc. FIG. 1 shows a schematic illustration of pMT-mGFc. This plasmid encodes a fusion polypeptide comprising the region spanning amino acids 44-173 of the mouse GITRL shown under GenBank Accession: NP_899247 and the Fc fragment derived from mouse IgG2.

The plasmid pMT-mGFc thus prepared was cotransfected with plasmids pGP and pE-eco contained in Retorovirus Packaging Kit Eco (Takara Bio Inc.) into HEK293T cells, and the transfectants were cultured for 2 days to obtain a cell supernatant, which was then filtered through a 0.45 µm filter (Milex HV, Millipore), thereby generating MT-mGFc/ECO retrovirus.

Example 2

Generation of Mouse GITRL-Fc Gene-Transfected Cells

Retronectin (Takara Bio Inc.) was used according to the protocol supplied by the manufacturer to infect methylcholanthrene (chemical carcinogen) induced mouse fibrosarcoma cells CMS 5 [Journal of Experimental Medicine, Vol. 146, pp. 720-734 (1977)] with the MT-mGFc/ECO retrovirus prepared in Example 1, thereby generating CMS5 cells transfected with the mouse GITRL-Fc gene. Subsequently, cloning was performed by limiting dilution, and mouse GITRL-Fc gene-transfected CMS5 cell clones 1 and 7 (hereinafter referred to as "clone 1" and "clone 7," respectively) were obtained.

Measurement of expression of mouse GITRL-Fc in the cloned cells was carried out by the following method: Mouse GITRL-Fc gene-transfected CMS5 cells were plated in a 96-well plate at a density of $2\times10^5$ cells/200 µl, and 2 µl of 10-fold dilution of Golgi Plug (BD Biosciences) was added after 10 hours. The cells were further cultured for 9 hours. The Cytofix/Cytoperm Kit (BD Biosciences) was used to fix the cells and permealized the membrane, and the cells were stained with anti-mouse IgG mAb-FITC conjugate (Caltag). The mouse GITRL-Fc expression in each cells was determined by flow cytometry. FIG. 2 shows the results of the measurements of mouse GITRL-Fc in the cells by flow cytometry: (a) non-transfected cells; (b) mouse GITRL-Fc gene-transfected bulk cells; and (c) clone 1. As shown in FIG. 2(*c*), the production of mouse GITRL-Fc was confirmed in mouse GITRL-Fc gene-transfected cell clones.

Example 3

Tumor-Bearing Experiment

Each clone 1 and 7 was subcutaneously injected into the right dorsal area of 8 to 10 week old BALB/c mice (CLEA Japan, Inc.) and 8 to 10 week old C.B-17/lcr-scid/scidJcr mice (CLEA Japan, Inc.) at a concentration of $1\times10^6$ cells/0.1 mL, and tumor size was determined every 2 to 3 days after the subcutaneous injection. The longest diameter and the shortest diameter of the tumor were measured, and the tumor size was calculated by multiplying the longest diameter by the shortest diameter. Five mice were used for each group.

FIG. 3 shows time-dependent changes in mouse tumor size in each mouse group. The horizontal axis indicates the number of days and the vertical axis indicates the product of the tumor size (the longest diameter×the shortest diameter: mm×mm). For each mouse GITRL-Fc gene-transfected CMS5 cell clone, while immunodeficient C.B-17/lcr-scid/scidJcr mice showed a continuous increase in tumor size, the tumor size was reduced in the BALB/c mice with normal immune function and almost no tumor was observed before day 17. The figure show the product of the diameters of the tumor transplanted in the right dorsal area of mices: filled circles represent the group of BALB/c mice transplanted with clone 1; filled triangles represent the group of BALB/c mice transplanted with clone 7; open circles represent the group of C.B-17/lcr-scid/scidJcr mice transplanted with clone 1; and open triangles represent the group of C.B-17/lcr-scid/scidJcr mice transplanted with clone 7.

Example 4

Confirmation of the Induction of Tumor-Specific Cytotoxic T Lymphocytes in the Tumor-Bearing Mice CMS5 or clone 1 as prepared in Example 2 was subcutaneously injected into the right dorsal area of 8 to 10 week old BALB/c mice at a concentration of $1\times10^6$ cells/0.1 mL. Splenocytes and their regional lymph node cell were collected at days 8 and 14 after the subcutaneous injection and a tetramer assay was carried out as follows: Epitope peptide 9m (SEQ ID NO: 5), from CMS5 tumor rejection antigen, was added to $5\times10^5$ cells of mouse mastocytoma cell line P1.HTR cells [Somatic Cell and Molecular Genetics, Vol. 11, pp. 467-475 (1985)] at a final concentration of 1 µM, and the cells were culture for 2 hours at 37° C. (9m peptide pulsed P1.HTR cells). These cells were mixed with the splenocytes at a ratio of 1:40, and these 9m peptide pulsed P1.HTR cells were also mixed with the regional lymph node cells and the splenocytes at a ratio of 1:40:8. The mixtures were co-cultured for one week, stained with a tetramer of 9m and mouse $H2/K^d$ ($9m/K^d$ tetramer-PE conjugate) (The Ludwig Institute Core Factory, Lausanne, Switzerland), and then analysed by flow cytometry.

Figure 4:
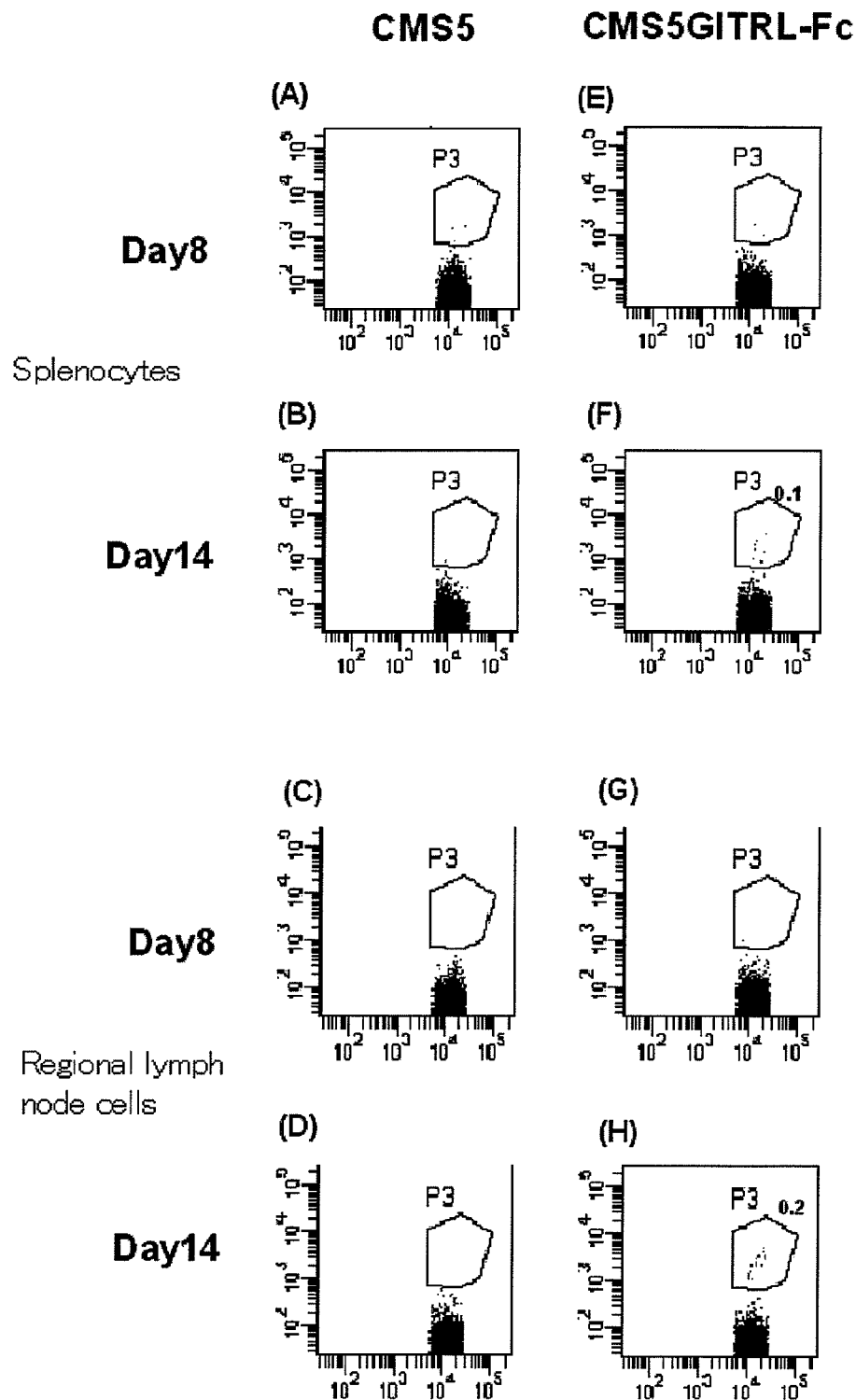
FIGS. 4A-H show the results of a tetramer assay.

FIG. 4 shows the results of the analysis by flow cytometry. The enclosed areas represent the cells reacted with the $9m/K^d$ tetramer-PE conjugate. As shown in FIG. 4 (A) to (D), no cells reacted with the $9m/K^d$ tetramer-PE conjugate were detected in all the splenocytes and the regional lymph node cells collected at days 8 and 14 in the mice subcutaneously injected with CMS5. In contrast, as shown in FIG. 4(E) to (H), the significant emergence of cells that reacted with $9m/K^d$ tetramer-PE conjugate was confirmed in both the splenocytes and the regional lymph node cells collected at day 14 in mice subcutaneously injected with clone1. Thus, it was confirmed that tumor-specific cytotoxic T lymphocytes against CMS5 were induced only in the clone1-bearing mice.

Example 5

Monitoring of Tumor Growth in CMS5GITRL-Fc-Bearing Mice Receiving Various Antibodies Clone 1 as prepared in Example 2 was subcutaneously injected into the right dorsal area of 8 to 10 week old BALB/c mice at a concentration of $1\times10^6$ cells/0.1 mL. In this treatment, 50 µg of anti-mouse CD4 antibody (Clone GK1.5) or 25 µl of anti-mouse CD8 antibody (Clone Lyt2.2) was administered via the orbital venous every 3 days for 2 weeks from one day before the subcutaneous injection, or 250 µg of anti-mouse CD25 antibody (Clone PC61) was administered once via the orbital venous a day before the subcutaneous injection. Tumor size was determined every 2 to 3 days after the subcutaneous injection in the same manner as described in Example 3. Three mice were used for each group.

Figure 5:
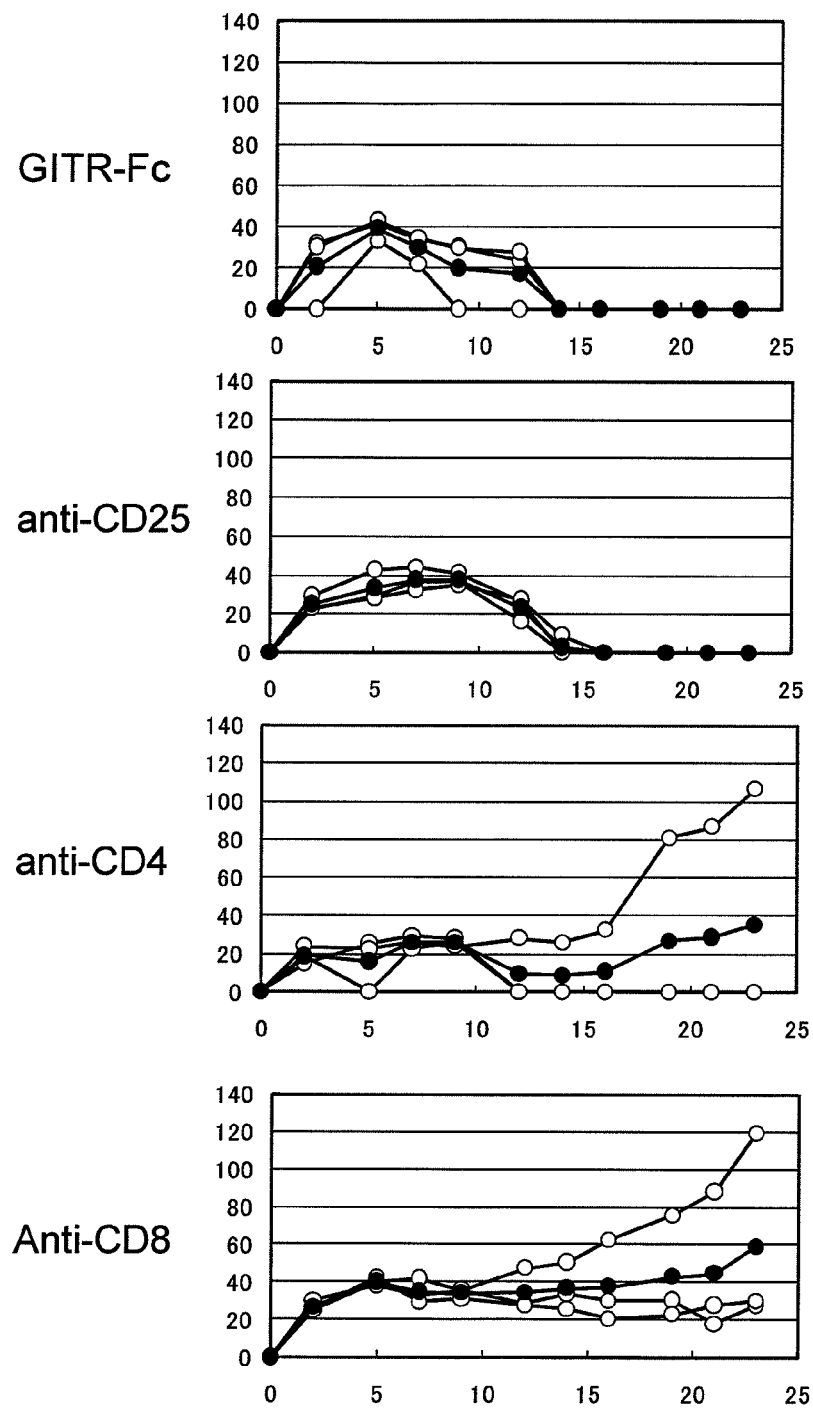
FIG. 5 shows chronological changes in mouse tumor size.

FIG. 5 shows time-dependent changes in mouse tumor size in each mouse group. The horizontal axis indicates the number of days and the vertical axis indicates the product of the tumor diameters (mm×mm). The open circles represent the results of each of the three mice, and the filled circles represent the mean values of the results. In FIG. 5, GITR-Fc shows the results from the mice given no antibody treatment, anti- CD25 indicates those from the mice administered with anti-mouse CD25 antibody, anti-CD4 indicates those from the mice administered with anti-mouse CD4 antibody, and anti-CD8 indicates those from the mice administered with anti-mouse CD8 antibody. The mice given no antibody treatment and the mice administered with anti-mouse CD25 antibody showed reduction in tumor size, and the tumor almost disappeared before day 15. In contrast, the mice administered with anti-mouse CD4 antibody and the mice administered with anti-mouse CD8 antibody showed continuous increase in tumor size in two of three mice in each group, indicating that both CD4-positive T cells and CD8-positive T cells are involved in the anti-tumor effect.

Example 6

Confirmation of the Induction of CMS5 Tumor Growth and Tumor-Specific Cytotoxic T Lymphocytes in the Mice Administered with Radiation-Inactivated MouseGITRL-Fc Gene-Transfected CMS5 Cells CMS5 inactivated by irradiation with 100 cGy X-rays or clone 1, prepared in Example 2, inactivated by irradiation with 100 cGy X-rays was subcutaneously injected into the right dorsal area of 8-10 week old BALB/c mice at a concentration of $5\times10^6$ cells/0.1 mL and, 7 days after, CMS5 was subcutaneously injected into the right dorsal area of the mice at a concentration of $1\times10^6$ cells/0.1 mL. Tumor size was determined every 2 to 3 days after the subcutaneous injection in the same manner as described in Example 3. Splenocytes and their regional lymph node cells were collected at day 14 after the subcutaneous injection and a tetramer assay was carried out in the same manner as described in Example 4.

FIG. 6 shows time-dependent changes in mouse tumor size in each mouse group; and the horizontal axis indicates the number of days and the vertical axis indicates the product of the tumor diameters (mm×mm). FIG. 7 shows the results of the tetramer assay. The mice administered with X ray irradiation-inactivated clone 1 showed inhibition of tumor growth, as compared with the mice administered with X ray irradiation-inactivated CMS5 (FIG. 6), and showed significant induction of tumor-specific cytotoxic T lymphocytes against CMS5 (FIG. 7). These results demonstrate that X ray irradiation-inactivated CMS5 GITRL-Fc retains the function as a vaccine.

Example 7

Monitoring of CMS5 Tumor Growth when X Ray Irradiation-Inactivated CMS5 GITRL-Fc was Administered to Mice Blocked with Various Antibodies Clone 1, prepared in Example 2, inactivated by irradiation with 100 cGy X-rays was subcutaneously injected into the right dorsal area of 8 to 10 week old BALB/c mice at a concentration of $5\times10^6$ cells/0.1 mL. To the mice, 50 µg of anti-mouse CD4 antibody (Clone GK1.5) or 25 µl of anti-mouse CD8 antibody (Clone Lyt2.2) was administered via the orbital venous every 3 days for 2 weeks from day 6, or 250 µg of anti-mouse CD25 antibody (Clone PC61) was administered once via the orbital venous at day 6. At day 7, CMS5 was subcutaneously injected into the right dorsal area of the mice at a concentration of $1\times10^6$ cells/0.1 mL. Tumor size was determined every 2 to 3 days after the subcutaneous injection in the same manner as described in Example 3.

Figure 8:
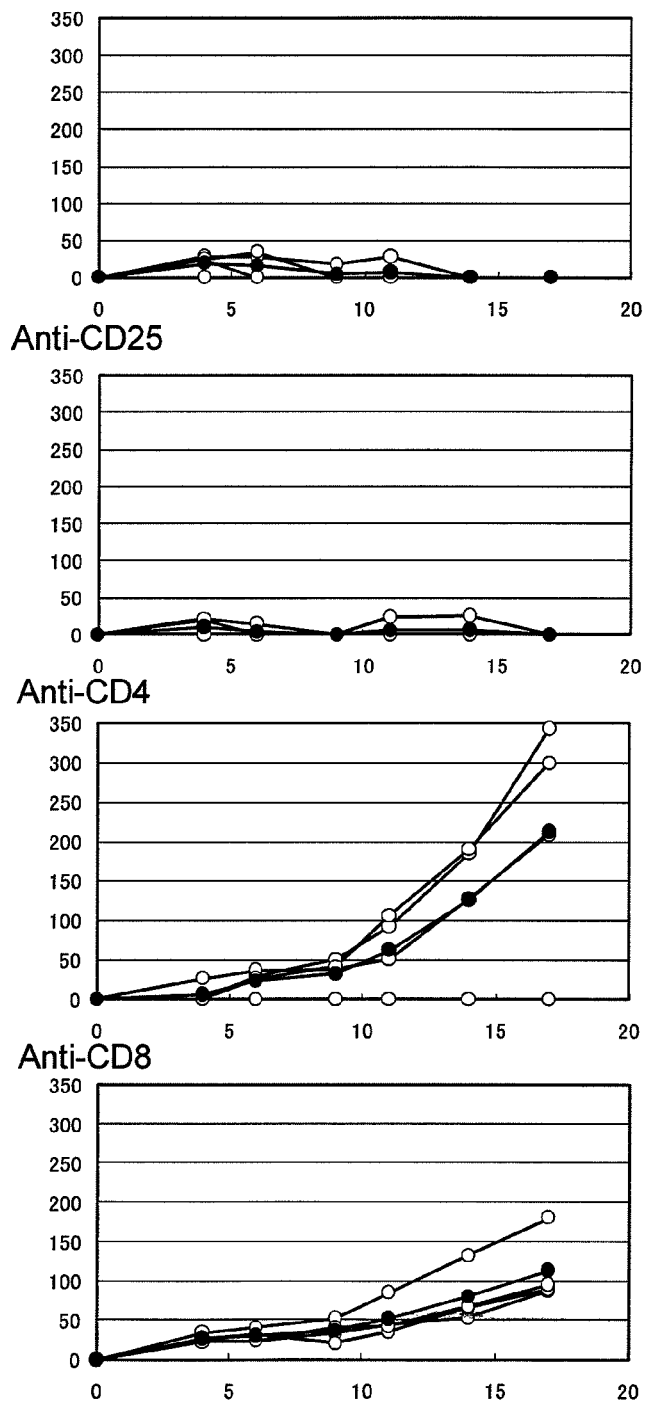
FIG. 8 shows chronological changes in mouse tumor size.

FIG. 8 shows time-dependent changes in mouse tumor size in each mouse group. In the figure, the horizontal axis indicates the number of days and the vertical axis indicates the product of the tumor diameters (mm×mm). The open circles represent the results of each of the three mice, and the filled circles represent the mean values of the results. In FIG. 8, GITR-Fc shows the results from the mice given no antibody treatment, anti-CD25 indicates those from the mice administered with anti-mouse CD25 antibody, anti-CD4 indicates those from the mice administered with anti-mouse CD4 antibody, and anti-CD8 indicates those from the mice administered with anti-mouse CD8 antibody. While the mice given no antibody treatment and the mice administered with anti-mouse CD25 antibody showed inhibition on the increase in tumor size, the mice administered with anti-mouse CD4 antibody and the mice administered with anti-mouse CD8 antibody showed continuous increase in tumor size in a significant manner, indicating that both CD4-positive T cells and CD8-positive T cells are involved in the vaccine effect of the X ray irradiation-inactivated CMS5 GITRL-Fc.

Example 8

Generation of Mouse GITRL-Fc Gene-Transfected Cells

Mouse colon cancer cell line CT26(ATCC CRL-2638) was infected with the MT-mGFc/ECO retrovirus, according to the method described in Example 2 to generate mouse GITRL-Fc gene-transfected CT26 cells. Subsequently, cloning was performed by limiting dilution, and mouse GITRL-Fc gene-transfected CT26 cell clone 21 (hereinafter referred to as "CT26-21") was obtained.

Plasmid vector pcDNA3.1 (Invitrogen) into which the GITRL-Fc gene is integrated was transfected into mouse melanoma cell line B16 (ATCC CRL-6475) using Lipofectamine 2000 (Invitrogen) to generate mouse GITRL-Fc gene-transfected B16 cells. Subsequently, cloning was performed by limiting dilution, and mouse GITRL-Fc gene-transfected B16 cell clones 2 and 3 (hereinafter referred to as "B16-2" and "B16-3," respectively) was obtained.

Example 9

Tumor-Bearing Experiment

CT26, CT26-21 (each $1\times10^6$ cells/0.1 mL), B16, B16-2 and B16-3 (each $5\times10^5$ cells/0.1 mL) were subcutaneously injected into the right dorsal area of 8 to 10 week old BALB/c mice (CLEA Japan, Inc.), and tumor size was determined every 2 to 3 days after the subcutaneous injection in the same manner as described in Example 3. Five mice were used for each group.

Figure 9:
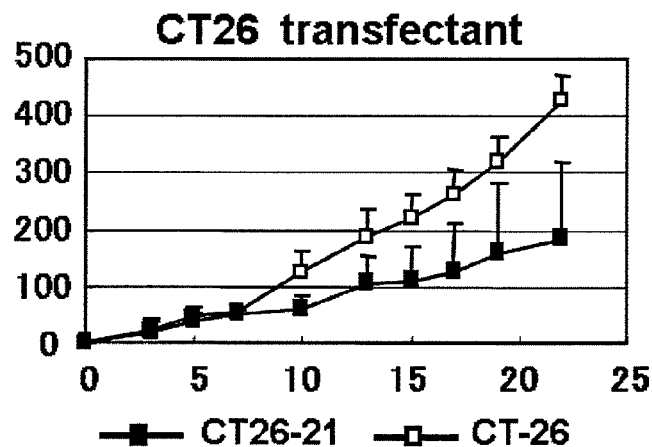
FIG. 9 shows chronological changes in mouse tumor size.
Figure 10:
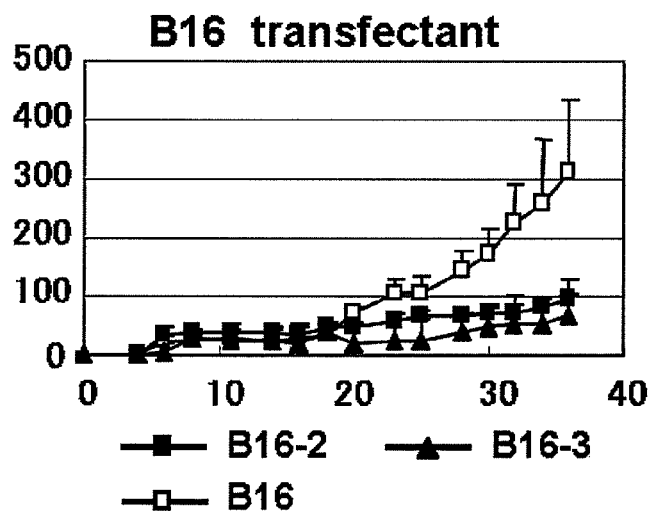
FIG. 10 shows chronological changes in mouse tumor size.

FIGS. 9 and 10 shows the time-dependent changes in mean mouse tumor size in each mouse group. The horizontal axis indicates the number of days and the vertical axis indicates the produce of the tumor size (the longest diameter×the shortest diameter: mm×mm). Both the mouse GITRL-Fc gene-transfected CT26 cell clone (CT26-21, represented by filled squares in FIG. 9) and the mouse GITRL-Fc gene-transfected B16 cell clones (B16-2 and B16-3, represented by filled squares and filled triangles, respectively, in FIG. 10) showed reduction in tumor size in the BALB/c mice with normal immune function, as compared with the control (represented by open squares in the figures). The results demonstrate the anti-tumor effect of GITRL-Fc in various cancer cells.

Example 10

Monitoring of the Capacity of T Cell Activation of GITRL-Fc

Figure 11:
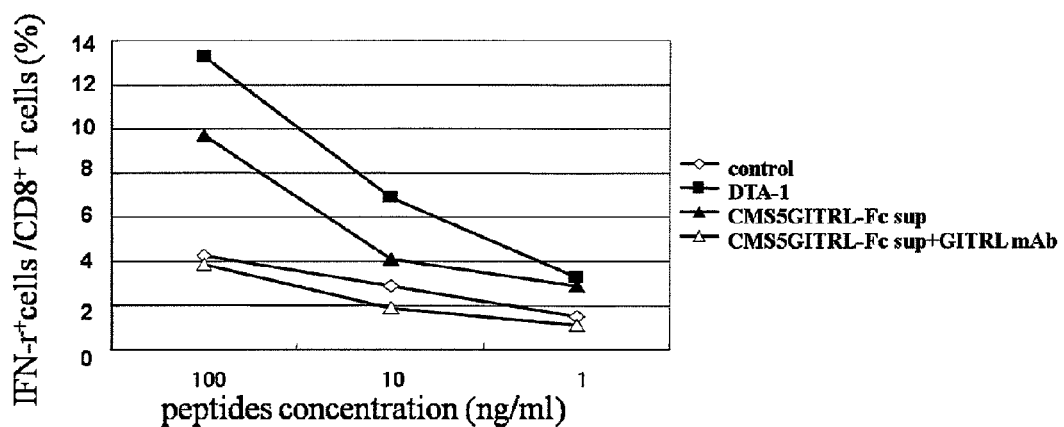
FIG. 11 shows T-cell activation.

CD8-positive T cells specific for the 9m peptide derived from the 9m peptide-specific TCR gene-transfected DUC18 mice ($3\times10^5$ cells) were mixed with $1\times10^6$ cells of splenocytes derived from wild-type BALE/c mice pulsed with 100 ng/ml, 10 ng/ml or 1 ng/ml of 9m peptide, and the mixture was incubated at 37° C. for 15 hours in each of the following media: RPMI1640 medium with 10% fetal calf serum (FCS) (used as the control in FIG. 11, represented by open squares); 10% FCS-supplemented RPMI1640 medium with DTA-1 (anti-GITR agonist antibody) at a concentration of 5 µg/ml (in the figure indicated as DAT-1, represented by filled squares); 10% FCS-supplemented RPMI1640 medium supplemented with 50 µl of the supernatant of the cultured mouse GITRL-Fc gene-transfected clone 1 cells, prepared in Example 2 (in the figure indicated as CMS5GITRL-Fc sup, represented by filled triangles); and 10% FCS-supplemented RPMI1640 medium supplemented with 50 µl of the supernatant of the cultured mouse GITRL-Fc gene-transfected clone 1 cells, prepared in Example 2, and with anti-GITRL antibody at a concentration of 5 µg/ml (in the figure indicated as CMS5GITRL-Fc sup+GITRLmAb, represented by open triangles). Intracellular IFN-γ in each DUC18 mice-derived CD8-positive T cells specific for the 9m peptide was stained with anti-IFN-γ antibody (BD Biosciences) and analysed by flow cytometry.

FIG. 11 shows the ratio of IFN-γ-positive cells contained in the CD8-positive cells in each sample at various peptide concentrations. Similarly to DTA-1, which stimulates GITR to activate effector cells, the supernatant of mouse GITRL-Fc gene-transfected cells was shown to induce IFN-γ production by activating CTL clones. The fact that anti-GITRL antibody inhibited the induction of IFN-γ production in the supernatant of mouse GITRL-Fc gene-transfected cells indicates that GITRL-Fc secreted from the mouse GITRL-Fc gene-transfected cells has the equivalent activity as αGITR agonist antibody and stimulates and activates GITR in T cells.

Example 11

Monitoring of the Induction Suppressive Effect of GITRL-Fc on Regulatory T Cells CMS5 or the mouse GITRL-Fc gene-transfected cells clone 1 as prepared in Example 2 (indicated as CMS5GLFc in FIGS. 12 and 13) was subcutaneously injected into the right dorsal area of 8 to 10 week old BALB/c mice at a concentration of $1\times10^6$ cells/0.1 mL. Splenocytes (spleen), regional lymph node cells (DLNs) and tumor-infiltrating lymphocytes (TILs) of CMS5 were collected at day 9 after the subcutaneous injection, and they were stained with anti-CD4 antibody (BD Biosciences), anti-Foxp3 antibody (e Biosciences), anti-CD8 antibody (BD Biosciences) and anti-CD25 antibody (BD Biosciences) and analysed by flow cytometry.

Figure 12:
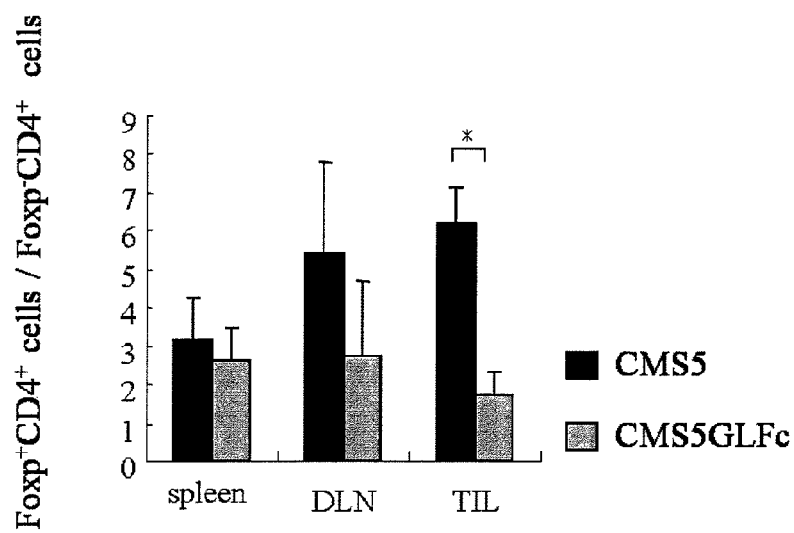
FIG. 12 shows the ratios of regulatory T cells.
Figure 13:
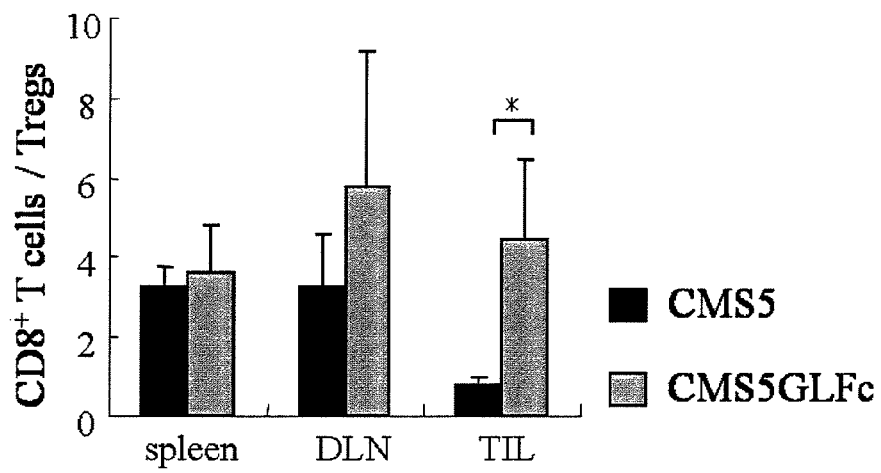
FIG. 13 shows the ratios of CD8-positive T cells.

FIG. 12 shows the ratio of CD4-positive, Foxp3-positive cells (regulatory T cells) to CD4-positive, Foxp3-negative cells in each tissue. FIG. 13 shows the ratio of CD8-positive cells to CD4-positive, Foxp3-positive cells (regulatory T cells).

As shown in FIG. 12, the mouse GITRL-Fc gene-transfected tumor cells showed significantly stronger suppression of the induction of regulatory T cells in the tumor-infiltrating lymphocytes than CMS5 and, as shown in FIG. 13, it was demonstrated that the proportion of CD8 cells increases relative to that of regulatory T cells.

Example 12

Monitoring of the Acquisition of Multifunctionality by T Cells by GITRL-Fc Expression CMS5 was subcutaneously injected into the right dorsal area of 8 to 10 week old BALE/c mice at a concentration of $1\times10^6$ cells/0.1 mL. Seven days later, the mice were grouped into: a group injected with $1\times10^6$ cells/0.1 mL of 9m peptide-specific CD8-positive T cells derived from DUC18 mice by tail vein injection (indicated as ACT in FIGS. 14 and 15); a group injected with $1\times10^6$ cells/0.1 mL of 9m peptide-specific CD8-positive T cells derived from DUC18 mice by tail vein injection and then subcutaneously injected with $1\times10^7$ cells/0.1 mL of radiation-inactivated CMS5 into the left dorsal area (indicated as ACT+CMS5 vac in FIGS. 14 and 15); and a group injected with $1\times10^6$ cells/0.1 mL of 9m peptide-specific CD8-positive T cells derived from DUC18 mice by tail vein injection and then subcutaneously injected with $1\times10^7$ cells/0.1 mL of the radiation-inactivated mouse GITRL-Fc gene-transfected cells clone 1 as prepared in Example 2 into the left dorsal area (indicated as ACT+CMS5 GLFc vac in FIGS. 14 and 15). The tumor size of each group of mice was determined every 3 to 5 days in the same manner as described in Example 3. At day 10, regional lymph node cells were collected and CD8-positive cells were stained with anti-IFN-γ antibody, anti-TNF-α antibody (BD Biosciences) and anti-CD107a antibody (e Biosciences) and analysed by flow cytometry.

Figure 14:
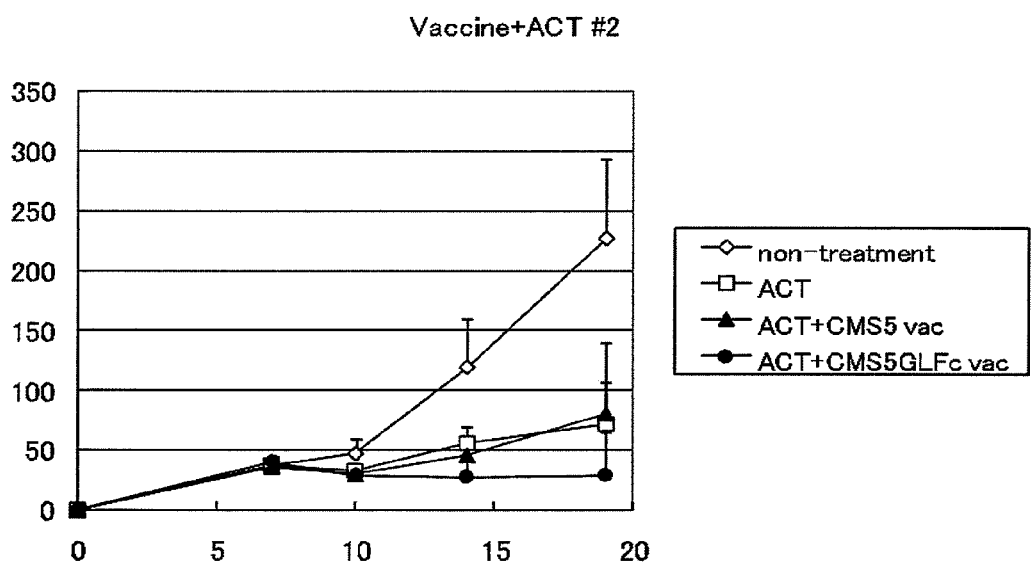
FIG. 14 shows chronological changes in mouse tumor size.

FIG. 14 shows the time-dependent changes in mean mouse tumor size in each mouse group. The horizontal axis indicates the number of days and the vertical axis indicates the product of the tumor size (the longest diameter×the shortest diameter: mm×mm). Tumor growth was nearly inhibited in the group administered with 9m peptide-specific CD8-positive T cells derived from DUC18 mice+the mouse GITRL-Fc gene-transfected cells, indicating that GITRL-Fc enhances the anti-tumor effect of tumor antigen-specific T cells.

Figure 15:
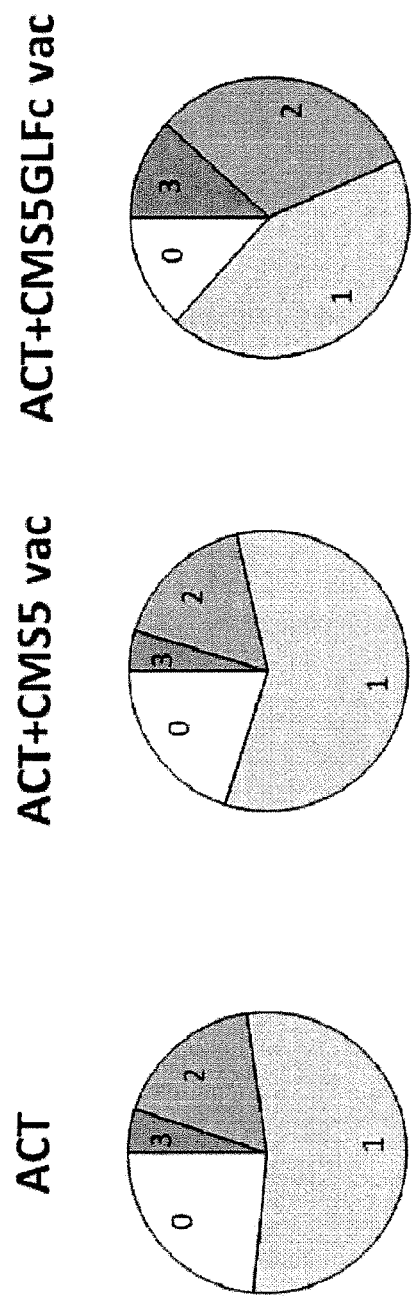
FIG. 15 shows the ratios of multifunctional cells.

FIG. 15 shows the proportions of the following types of cells present in the 9m peptide-specific CD8-positive cells transferred into lymph node: the cells showing all the three functions of IFN-γ production, TNF-α production and CD107a expression (the indices for the capacity of cytotoxic granulocyte production) (Type 3); the cells showing two functions (Type 2); the cells showing a single function (Type 1); and the cells without any function (Type 0). The group administered with 9m peptide-specific CD8-positive T cells derived from DUC18 mice+the mouse GITRL-Fc gene-transfected cells has a higher ratio of the cells showing three or two functions, compared with the other groups, indicating that GITRL-Fc allows tumor antigen-specific effector T cells to acquire multifunctionality with high efficiency.

Example 13

Generation of an Adenovirus Vector Expressing Mouse GITRL-Fc

The vector pMT-mGFc prepared in Example 1 was cleaved with endonucleases NotI and SalI (Takara Bio Inc.) and subjected to agarose gel electrophoresis, and an about 1.2 kbp fragment containing the mouse GITRL-Fc sequence was recovered from gel. The fragment recovered was blunted using a DNA Blunting Kit (Takara Bio Inc.) and then ligated into the SwaI site of cosmid vector pAxCAwtit2 (Takara Bio Inc.). The recombinant DNA thus obtained was transformed into *E. coli* DH5 alpha (Takara Bio Inc.) using Gigapack III XL Packaging Extract (Agilent Technologies), and a transformant was selected in ampicillin-supplemented LB medium. This tranformant was further cultured to prepare cosmid DNA, which was designated "pAxCAwtit2-mGITRL-FcA."

Then, TransIT-293(Mirus Bio LLC) was used to transform HEK293 cells with pAxCAwtit2-mGITRL-Fc cleaved with endonuclease BspT104I (Takara Bio Inc.). The transformant thus obtained was cultured, and the culture was sonicated for fragmentation. The concentrated culture supernatant containing the GITRL-Fc-expressing adenovirus vector AxCA-mGITRL-Fc was recovered and the primary virus solution was obtained.

The primary virus solution was used to infect HEK293 cells, which were then cultured. The culture was sonicated and the supernatant was recovered, thereby obtaining the secondary virus solution. The third and fourth virus solutions were obtained by the same operation.

In a similar manner, the fourth virus solution was prepared from cosmid vector pAxCAwtit2-AcGFP, in which the AcGFP gene is cloned from pAcGFP1 Vector (Clontech). The adenovirus vector contained in this virus solution is designated AxCA-AcGFP.

Finally, an Adeno-X™ Rapid Titer Kit (Clontech) was used to determine the virus titer of the two different fourth virus solutions.

Example 14

Infection of Adenovirus Vector to Mouse Tumor Cells

The fourth virus solutions of each adenovirus vectors prepared in Example 13 were used to infect methylcholanthrene (chemical carcinogen) induced mouse fibrosarcoma cell line CMS5 and mouse colon cancer cell line CT26 at MOIs (multiplicity of infection: the amount of infectious virus per cell) of 10 and 50, and the cells were cultured for 2 days. TO confirm the efficiency of the infection, each of the tumor cell lines infected with the fourth virus solution of AxCA-AcGFP were analyzed by flow cytometry. As a result, for CMS5 and CT26 infected at a MOI of 10, 72.2% and 57.1% of the CMS5 and CT26 cells, respectively, were confirmed to have been infected by virus. For CMS5 and CT26 infected at a MOI of 50, 99.1% and 94.9% of the CMS5 and CT26 cells, respectively, were also confirmed to have been infected by virus. Each of the tumor cell lines infected with AxCA-mGITRL-Fc and AxCAwt2 at a MOI of 50 were used in the subsequent examples.

Example 15

Confirmation of Tumor Growth in the Mice Administered with Adenovirus Vector-Infected Mouse Tumor Cells AxCA-mGITRL-Fc-infected CMS5, noninfected CMS5, AxCA-mGITRL-Fc-infected CT26 and noninfected CT26 prepared in Example 14 were subcutaneously injected into the right dorsal area of 8 to 10 week old BALB/c mice (CLEA Japan, Inc.) at a concentration of $1\times10^6$ cells/0.2 mL, and the tumor size was determined every 2 to 3 days after the subcutaneous injection in the same manner as described in Example 3. Five mice were used for each group.

The mean±standard deviation size ((the longest diameter+ the shortest diameter/2: mm) of the tumor diameter at day 15 was 11.74±3.49 for AxCA-mGITRL-Fc-infected CMS5, 15.59±1.84 for noninfected CMS5, 5.76±4.65 for AxCA-mGITRL-Fc-infected CT26, and 13.26±3.45 for noninfected CT26.

The mouse GITRL-Fc gene-transfected cells showed reduction in tumor size, indicating the inhibitory effect of the GITRL-Fc-expressing adenovirus vectors on tumor growth in various tumor cells.

INDUSTRIAL APPLICABILITY

The cells, therapeutic agent, prophylactic agent and treatment method of the present invention may be applied to the treatment or prevention of diseases, including tumors and infections. They are capable of potently inducing the immune system.

SEQ ID NO:1: mGITRL-FLF primer
SEQ ID NO:2: mGITRL-FLR primer
SEQ ID NO:3: mGF5 primer
SEQ ID NO:4: mFc3 primer
SEQ ID NO:5: Epitope petide 9m

The invention claimed is:

1. A pharmaceutical composition comprising an excipient and an immune cell capable of expressing an exogenous Glucocorticoid-Induced Tumor necrosis factor Receptor Ligand (GITRL) derivative, wherein said GITRL derivative is a fusion protein consisting of amino acids 50-177 of SEQ ID NO: 6 fused to an Fc fragment of an immunoglobulin, wherein the composition comprises $1\times10^3$ to $1\times10^{11}$ cells/mL of said immune cell.

2. The pharmaceutical composition of claim 1 wherein said immunoglobulin is IgG2.

3. The pharmaceutical composition of claim 1 wherein said composition comprises $1\times10^4$ to $1\times10^{10}$ cells/mL of said immune cell.

4. The pharmaceutical composition of claim 1 wherein said composition comprises $1\times10^5$ to $1\times10^9$ cells/mL of said immune cell.

5. A pharmaceutical composition comprising an excipient and an inactivated tumor cell capable of expressing an exogenous Glucocorticoid-Induced Tumor necrosis factor Receptor Ligand (GITRL) derivative, wherein said GITRL derivative is a fusion protein consisting of amino acids 50-177 of SEQ ID NO: 6 fused to an Fc fragment of an immunoglobulin, wherein the composition comprises $1\times10^3$ to $1\times10^{11}$ cells/mL of said inactivated tumor cell.

6. The pharmaceutical composition of claim 5 wherein said immunoglobulin is IgG2.

7. The pharmaceutical composition of claim 5 wherein said composition comprises $1\times10^4$ to $1\times10^{10}$ cells/mL of said inactivated tumor cell.

8. The pharmaceutical composition of claim 5 wherein said composition comprises $1\times10^5$ to $1\times10^9$ cells/mL of said inactivated tumor cell.

\* \* \* \* \*